United States Patent [19]
Haris

[11] Patent Number: 4,787,906
[45] Date of Patent: Nov. 29, 1988

[54] CONTROLLED TISSUE GROWTH AND GRAFT CONTAINMENT

[76] Inventor: Andras G. Haris, No. 2 Weirwood Rd., Radnor, Pa. 19087

[21] Appl. No.: 20,986

[22] Filed: Mar. 2, 1987

[51] Int. Cl.$^4$ .............................................. A61F 2/28
[52] U.S. Cl. ................................... 623/16; 433/201.1
[58] Field of Search ............... 433/173, 174, 175, 176, 433/201.1, 215; 128/92 YG, 92 YR, 92 YQ; 623/16, 10

[56] References Cited

U.S. PATENT DOCUMENTS

| | | | |
|---|---|---|---|
| 2,644,231 | 8/1951 | Brennan | 32/2 |
| 3,849,805 | 11/1974 | Leake et al. | 3/1 |
| 3,953,566 | 4/1976 | Gore | 264/288 |
| 4,097,935 | 7/1978 | Jarcho | 3/1.9 |
| 4,187,390 | 2/1980 | Gore | 174/102 |
| 4,430,760 | 2/1984 | Smestad | 623/10 |
| 4,542,539 | 9/1985 | Rowe, Jr. et al. | 623/16 |
| 4,629,464 | 12/1986 | Takata et al. | 623/16 |
| 4,657,548 | 4/1987 | Nichols | 623/10 |

OTHER PUBLICATIONS

Kent et al., "Correction of Alveolar Ridge Deficiencies JADA Dec. 1982".
Coors Biomedical Co. "Are You Experiencing GAPS in Your Practice?".
W. L. Gore & Associates, Inc., "Gore-Tex Patch" Jul., 1985.
Calcitek, Inc., "A Simple Effective Solution to Alveolar Bone Restoration" Jul. 1985.
Interpore International, "The Nature of Interpore" 1985.
Interpore International, "Clinical Case Reports" May, 1985 Piecuch, et al.
Interpore International, "A New Technology for Ridge Reconstruction Has Taken Shape" Jun. 1985.

*Primary Examiner*—Samuel Scott
*Assistant Examiner*—Noah Kamen
*Attorney, Agent, or Firm*—Eugene Chovanes

[57] ABSTRACT

A device and technique for restoring the alveolar ridge of the human jawbone in the edentulous state. Such device involves an inert, porous tube which contains granules whereby when the device is in place on the ridge, tissue growth occurs from living bone through the porous tube inwardly or outwardly from the granular filler. The tube prevents the granules from migrating.

6 Claims, 3 Drawing Sheets

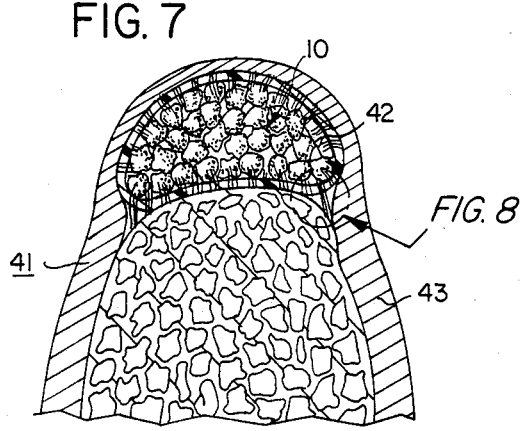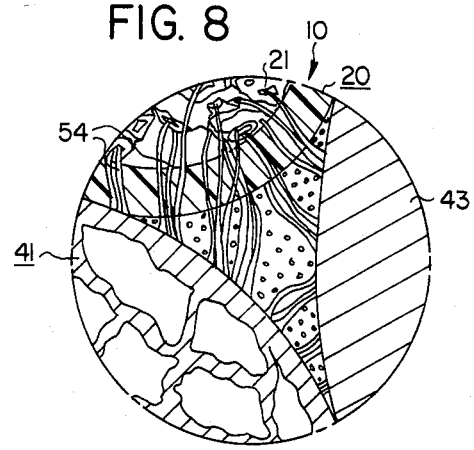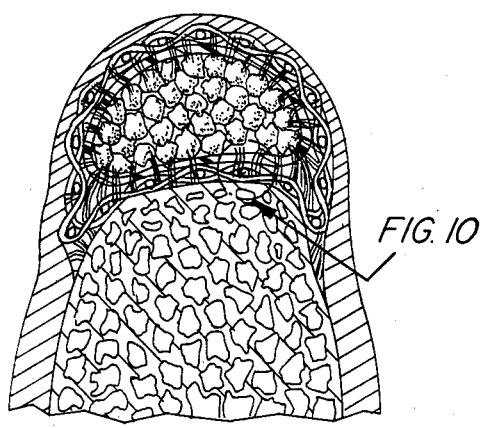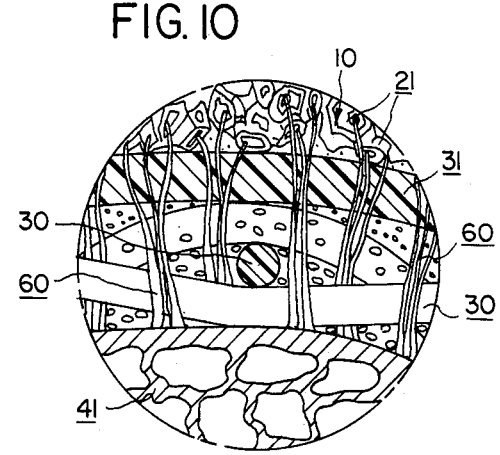

CONTROLLED TISSUE GROWTH AND GRAFT CONTAINMENT

BACKGROUND OF THE INVENTION

Field of the Invention

This invention generally relates to controlled tissue regeneration in humans. In particular, it deals with restoring the teeth-supporting portion of the jawbone (alveolar ridge) when the teeth have been extracted (edentulous state).

The Problem

In humans, teeth arise from that part of the jawbone known as the alveolar ridge. The state in which teeth formerly present are missing from the alveolar ridge is known as the edentulous state.

When useful teeth are in place, the alveolar ridge generally remains integral, supportive and healthy. When teeth are extracted, the bone shrinks, or resorbs. There is bone reduction, sometimes known as "disuse atrophy." The load from dentures resting on the ridge contributes to such reduction.

The resorbed alveolar ridge leaves a functionally and cosmetically deficient site; functionally, because there is not adequate surface to support a denture, and aesthetically because the facial appearance is distorted.

After tooth extraction, what was once a defined ridge becomes a relatively flat, undefined structure.

The condition is not desirable, because the patient's facial structure becomes distorted. The patient gets old looking. The mouth area becomes shrunken.

More importantly, the ridge is now incapable of supporting dentures or false teeth. The dentures become ill-fitting. The dentures probably also contribute to the problem. The dentures exert pressure and the pressure probably contributes to resorption.

The condition appears to be worse on the lower jaw than on the upper jaw. If artificial augmentation of the jawline is attempted utilizing synthetic granulated bone graft, the problem of migration is more extenuated in the lower jaw, possibly because of gravity.

Prior Efforts to Remedy the Problem

Bone grafts have been tried, but this requires extensive surgery and healing, with the results often being unsatisfactory.

Titanium anchors in the form of plugs or screws have also been placed in the lower jaw. This too requires extensive surgery and these anchors often become loose.

There have been extensive past efforts using a technique and composition wherein granulate ceramic material has been deposited over the ridge beneath the skin, by surgical technique. These granules are of a hydroxyapatite composition. They can be in granular form or in the form of granules formed into blocks. See U.S. Pat. No. 4,629,464 issued Dec. 16, 1986 for an example of such a product.

The granules themselves which are laid on top of and along the ridge are unsatisfactory because they migrate, and do not stay in place along the ridge to provide and compensate for resorption. The blocks likewise have not proven satisfactory, generally, since they are relatively fragile and break down and again there is migration. The blocks also being relatively rigid in form, slip off the ridge and do not provide a stable ridge restoration. Also, blocks involve a relatively difficult surgical technique for insertion.

SUMMARY OF THE PRESENT INVENTION

The object of the present invention is to maintain the height and the contour of the alveolar ridge, to provide suitable support for dentures, to preserve and enhance the facial appearance of an individual, and to maintain the upper and lower jawbones so that they articulate together properly.

After the teeth are extracted and the alveolar ridge heals, an implant of a flexible, porous, inert, tubular material containing a loose fill of inert, porous particles is positioned along the ridge and sewn in place.

The tube permits tissue fibers to pass through the tube from the underlying bone into the particle matrix and form a growth through the matrix. The porous tube contains and positions the loose particles and prevents the particles from migrating, particularly before substantial tissue regeneration occurs.

In an alternative embodiment, a second, relatively loose woven or knit outer tube is used over the inner tube. This permits relatively rapid tissue growth into the outer tube which quickly positions the device in place. Then a slower, more selective tissue growth occurs through the less porous inner tube into and about the particle matrix.

Since the device is flexible, comprising a flexible tube containing loosely filled particles, the device readily conforms to the contour of the ridge.

As an alternative, a shorter length tube containing particles can be inserted immediately after extraction into the socket for alveolar ridge maintenance, and the skin flap closed over the implant.

The device can be placed in position by a technique using a tunneling tool.

DESCRIPTION OF THE DRAWINGS

FIG. 7 is a greatly enlarged fragmentary transverse sectional view taken on the line 7,7 of FIG. 6, showing the porous, flexible tube with its associated granules after having been surgically implanted along the jawbone ridge in accordance with the method of use of this invention and showing the tissue growth.

FIG. 8 is an area within the dot-and-dash circle of of FIG. 7, greatly enlarged. This shows more clearly the tissue growth through the porous tube wall and into the granules contained within.

FIG. 9 is a view similar to FIG. 7, but showing the use of one double concentric tube shown in FIG. 4.

FIG. 10 is a view similar to FIG. 8, utilizing the double concentric tube configuration of FIG. 4.

FIG. 11 is a greatly enlarged perspective view of a generally cubical fragment cut from a single granule showing its great porosity allowing the intergrowth of new tissue.

DETAILED DESCRIPTION OF THE INVENTION

Figure 1:
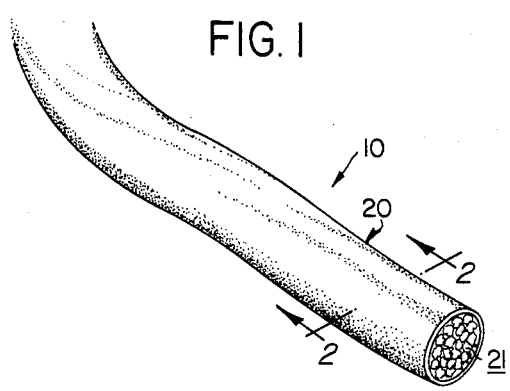
FIG. 1 is an enlarged fragmentary perspective view of the device of the invention.

FIG. 1 is a prospective view of the device 10 of the invention which consists essentially of a flexible outer closed bag or tube 20, and a granulate portion 21. The tube 20 itself is of a porous, inert nature of a type which would permit tissue movement through its pores inwardly from outside the tube, but which prevents migration of the granules outwardly through the tube.

Figure 2:
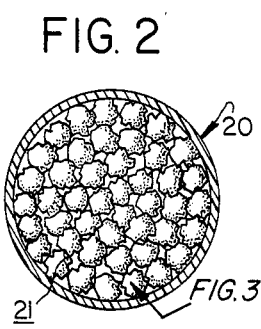
FIG. 2 is an enlarged sectional view taken on the line 2,2 of FIG. 1, showing the details of the tubular member and its associated granules more clearly.
Figure 3:
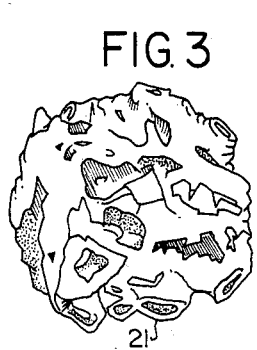
FIG. 3 is a greatly enlarged pictorial view of one of the porous granules that fill the flexible tube of this invention, and identified in FIG. 2 as FIG. 3.

As seen in FIG. 2, the granules 21 occupy the entire interior of the tube. Preferably, the tube is loosely filled so that the device can readily conform to the alveolar ridge contour. The granule itself as seen in FIG. 3 has an irregular surface and of itself, again, is inert. Such granules may be, for instance, of a type set forth in U.S. Pat. No. 4,629,464 which shows and explains in detail a sintered microporous, hydroxyapatite material. Such granules are well known commercially and are non-resorbable and commonly used as bone grafting material for alveolar ridge augmentation. The porous hydroxyapatite ceramic granules can be of, for instance, from 18 to 40 mesh. These granules in place permit bony ingrowth for improved stability of the augmented alveolar ridges.

The granules 21 are kept in place by the outer tube 20 which is flexible, both longitudinally and circumferentially. The material from which tube 20 is formed is porous and of an inert composition.

A suitable material for the tube 20 may be an expanded polytetrafluoroethylene material of the type, for instance, used in cardio-vascular patches in human surgery. Another type of suitable material is polypropylene in mesh form.

Such material is used in cardio-vascular patching for cardiac, great vessel, and peripheral vascular reconstructions. One commercial trade name for such material is Gore-Tex. The material in tube form can be obtained commercially and can be of a standard 6, 8 or 10 mm diameter. The cross sections of the tubes are shown greatly enlarged in the drawings. A suitable granule 21 could be, for instance, 0.75 mm in its largest dimension. The tube 20 is desirably loosely filled. The tube 20 in effect is filled with small granules which will provide a porous inner space wherein tissue will pass through from the outside of the tube into the porous granule arrangement.

It should be borne in mind that it is necessary for the material of the tube 20 to be thin-walled, porous and permit movement of tissue ingrowth through the walls of the tube while preventing migration of the granules.

Figure 5:
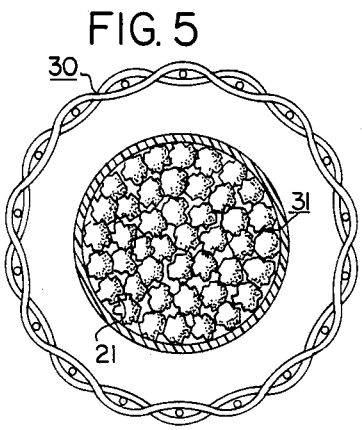
FIG. 5 is an enlarged sectional view taken on the line 5,5 of FIG. 4 similar to FIG. 2, showing in greater detail the construction of the concentric double tubes.

In an alternative embodiment of the device of the invention, there is shown a concentric outer closed bag or tube 30 over an inner bag or tube 31, with the granules 21 contained within the inner bag 31. In FIG. 5, I show substantial space between the bags merely for illustrative purposes, but in actual construction, the bags are adjacent to one another and in contiguous relationship - abutting relationship.

Figure 4:
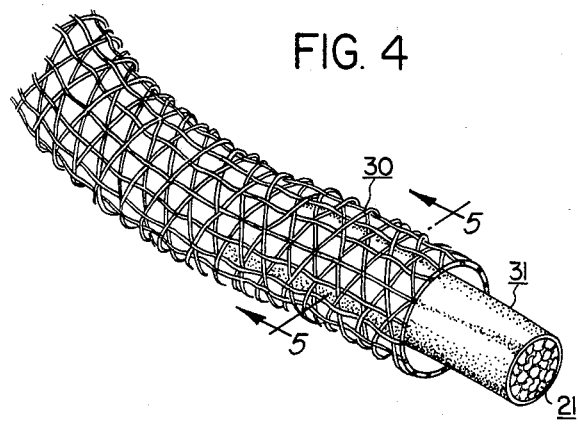
FIG. 4 is an enlarged fragmentary perspective view of an alternative embodiment of the invention.

In FIG. 4, I show the inner and outer bags 30 ad 31 in a perspective fragment of the tube. In FIG. 5, I show a cross section of such device taken on the line 5,5 of FIG. 4. Again, there is space shown between the inner bag 31 and the outer bag 30 merely for illustrative purposes. The fit between bags 30 and 31 will desirably be snug and one bag will in fact rest concentrically within another bag, and the inner bag will be loosely filled with granules 21.

In the embodiment of FIGS. 4 and 5, the outer bag 30 is of a greater porosity than the inner bag 31.

The outer bag 30 is desirably of an open, loose construction such as a knit or open weave and of a monofilament material which is inert. The outer bag 30 being of an open mesh permits rapid growth through its walls of tissue which quickly anchors the entire unit in its position on the alveolar ridge without necessarily having tissue growth into the granules. Tissue growth through the inner bag will be slower and finer due to its tight porosity. Thus, the construction of FIGS. 4 and 5 will permit relatively rapid overall positioning on the device on the ridge, while the inner bag will permit a slow, gradual and desirable growth within the bag over and through the granular particles.

It should be borne in mind that the particles, as well known, have pores within them, as particularly seen in FIG. 11.

In the embodiment of FIGS. 4 and 5, the bag or tube 31 is of the same construction as the bag or tube 20 in FIG. 1. In effect, the embodiment of FIG. 4 is the embodiment of FIG. 1, with an additional, concentric, open, porous weave bag 30 as seen in the drawings.

Figure 6:
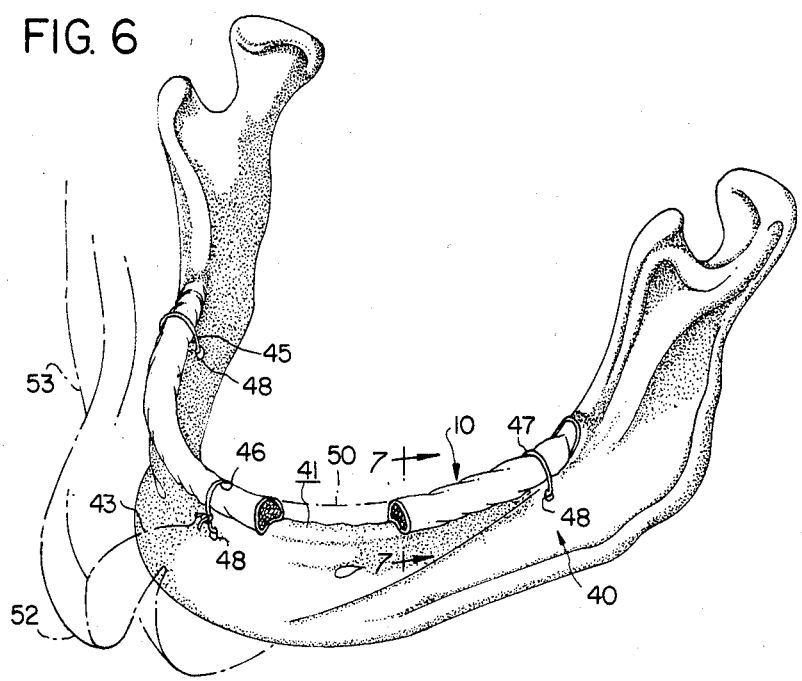
FIG. 6 is an enlarged pictorial view of the lower jawbone in the edentulous state, showing the device in position.

In FIG. 6, the device of the invention is shown in place on the lower human jawbone. The jawbone 40 in the area of the alveolar ridge 41 has substantially resorbed prior to the application of the device of the invention. Such resorption of the alveolar ridge occurs during healing after teeth extraction. The sockets left after the extraction are somewhat filled with tissue growth, and the original alveolar ridge line recedes, or melts, so that a lower, relatively continuous ridge line occurs, although the ridge may be somewhat generally lower in the front than in the back.

Where a double tube arrangement is used, it may be desirable to have selective tissue growth. The more open outer tube 30 would permit a more dense tissue to position and securely hold the entire device, while the inner tube 31 will permit a more selective tissue to enter into the granular material to form a growth therein. The different types of tissue growth grow with different speeds, so that a relatively quick growth can occur by virtue of the density of tube 30 and then a slower, more selective growth through tube 31.

Such rapid outer growth avoids the necessity for a multiplicity of sutures since a quick and continuous anchoring is created along the alveolar ridge. The bony ridge itself is show in FIG. 7 at 41. FIG. 7 is a cross section along the line 7,7 in FIG. 6. The ridge 41 has receded to a relatively uniform height throughout the ridge at 42. The overlying skin tissue or gum 43 has grown over the ridge 41. Between gum or tissue 43 and bone 41, the device 10 of the invention is anchored in place by sutures 45, 46 and 47. The sutures optionally can be passed through a hole 48 drilled through the ridge 41 and tied in place. Sutures are of any acceptable surgical type. The device 10 in such a condition as shown in FIG. 6 extends completely along the ridge with the skin 43 over the top thereof, resulting in the structure as shown in FIG. 7.

The outer skin is shown in dot-and-dash outline in FIG. 6 for greater clarity. Also, a portion of the device 10 is broken away at 50 to show the alveolar ridge with the device of the invention positioned thereon. Also shown in FIG. 6 in phantom outline are a lower lip 52 and face skin 53 to orient the jawbone 40.

FIG. 8 is a greatly enlarged view of the circled area designated FIG. 8 in FIG. 7, showing in greater clarity the relationship between skin 43, bone 41 and device 10 with the tube and granules 21. Of special significance in FIG. 8 is the tissue growth from bone 41 through pores of bag 20 into granules 21 by vascular filaments or fibers 54. Such FIG. 8 shows clearly the fibrobascular invasion into the granules from the living bone.

The fibrovascular invasion through the pores of the tube 20 into the granules 21 are such that there is a regeneration of cortical bone as osteons, in the well known prior art manner. The granules provide a biomatrix as a bone substitute that mimics the microstructure of natural bone. When placed next to viable bone, it provides a scaffold, or matrix, for the incorporation of connective tissue and bone similar to an autogenous graft. As a matter of fact, the filler can be resorbable synthetic bone graft, or any type of autogenous graft, or mixture thereof.

Where autogenous bone graft containing active cells is used, tissue growth can occur from the graft outwardly through the tube to the surrounding supporting structure.

In such biomatrix, the pores are connected one to another to form continuous, uniform channels with no dead ends. This intricate labyrinth of interconnected pores provides optimal permeability and a high surface area that encourages tissue ingrowth, vascularization, and deposition of new bone. Such pore structure is shown in FIG. 11.

In FIG. 9, I show a cross section which is equivalent to FIG. 7 of the embodiment of FIGS. 4 and 5, the double tube embodiment in place.

FIG. 10 is a greatly enlarged portion of FIG. 9 which is designated thereon as FIG. 10.

In FIG. 10 there is seen bone 41, granules 21, inner tube 31 and open weave or knit outer tube 30 in position. The vascular fibers 60 provide little obstacle to relatively rapid movement through tube 30 since the relatively large size of the weave or knit, with its open structure, is much greater than the fiber size. There is a relatively thicker growth through bag 30 which relatively quickly positions the entire device 10. However, the same end result is eventually achieved through inner bag 31 as seen in FIG. 8 wherein fibers grow into the granular matrix and weave and wind therein.

As described above, selective tissue growth, both as to type and speed, can be achieved by selectively using different mesh, or porosity tube material. Additional concentric outer tubes, for instance, three or more, can be used of different porosity, to further curtail tissue growth.

Figure 12A:
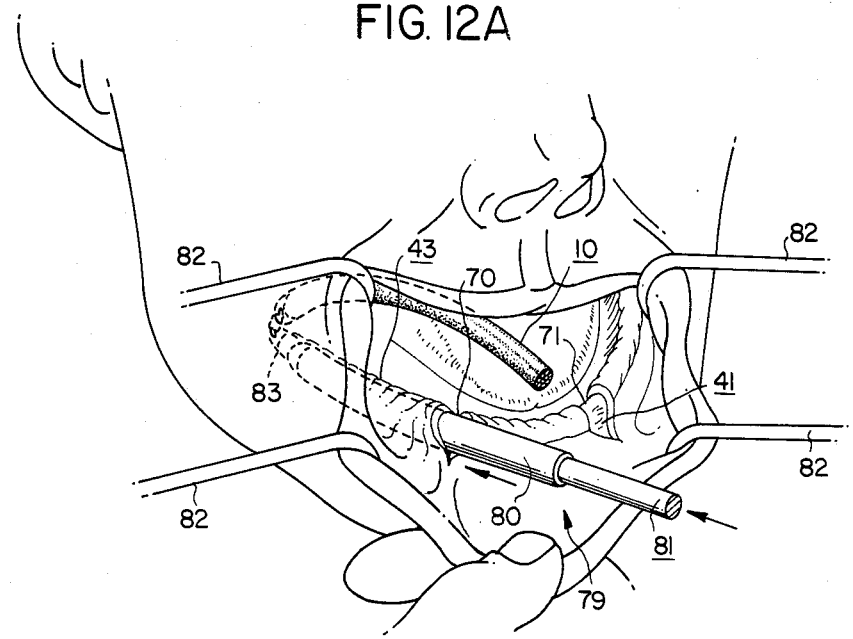
FIG. 12A is a fragmentary perspective view of the patient's head and mouth, with the flesh and lips of the patient being distended, in the first phase of one technique, for inserting the device in a patient.
Figure 12B:
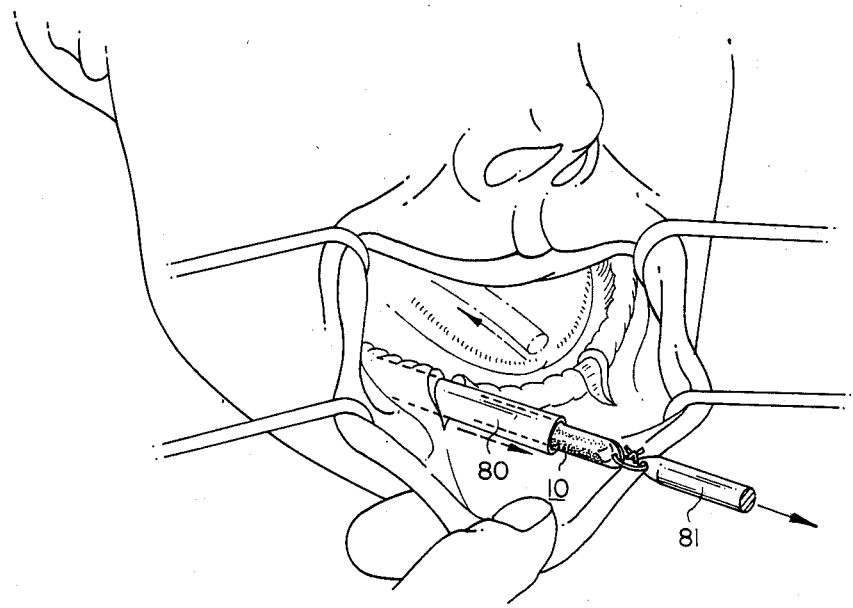
FIG. 12B is similar to FIG. 12A, showing a later phase of the insertion.

One technique of insertion is shown in FIGS. 12A and 12B. Suitable cuts are made at 70, 71. Initial cuts are made at 70 and 71, symmetrically on either side of the center of the alveolar ridge, suitably one-third of the distance of the entire ridge, apart.

In the first movement, a tunneling tool having a rigid or semi-rigid outer tubular portion 80 which may be of metal or sterilizable plastic having optionally a curve to conform to the ridge curve, or flexible enough to thread along the ridge, is used. The tube 80 has an inner slidable, longitudinal member 81 which can readily telescope within tube 80 and extend all along the entire length of tube 80. The tube 80 and rod 81 telescoping together form the tunneling tool 79 Tube 80 with rod 81 inserted therein is forced rearwardly through cut 70 along the alveolar ridge to the rear of jaw, as seen in FIG. 12A. The mouth is held open in known surgical procedure by suitable retracting instruments 82. The mouth and facial structure, including the tongue, are shown but not designated in the figures to provide clarity of explanation.

The tunneling tube has a point 83 and a suitable opening 84 at the apex of the point. Tube 80 is forced along ridge 41 until it is positioned to the extremity as seen in FIG. 12A.

Tube 80, although pointed, has enough of an opening 83 to permit inner rod 81 to be selectively pushed through opening 83 at the desired location wherein rod 81 pierces the outer skin. A surgical slit at that point could also be made. The device 10 of the invention is tied to a hole at the end of rod 81, and the entire bag or device 10 is pulled back by means of rod 81 through outer rigid tube 80 which is left in place as seen in FIG. 12B. The trailing end of device 10 is then anchored to ridge 41 at 48 after being pulled into tube 80 as shown in FIG. 6, with suture 45. Outer tube 80 is then withdrawn in the direction of the dashed arrow as shown in FIG. 12B.

The procedure is then repeated in the center segment 85 with tee tunneling tube and telescoping rod 80 and 81 being inserted from the slit 71. The procedure is repeated from slit 71 wherein the bag portion is threaded underneath the gum in the same manner as the first portion. Finally, if one bag is used, an additional slit will have to be made at the end thereof, at the right extremity as seen in FIG. 12B.

In the alternative, separate tubes may be used for each of the segments so that the threading on the right portion of the ridge as seen in FIG. 12 can take place in mirror image fashion from that on the left portion.

The tubes are suitably anchored as seen in FIG. 6 and the cuts 70 and 71 are sutured in proper surgical fashion.

It should be understood that other suitable methods may be used to place the devices in position, including extending the longitudinal slit above the alveolar ridge with proper suturing thereafter.

Also, it may be desirable to somewhat score the ridge along the ridge line to provide a more suitable anchoring trough for the device. Generally, however, the bone 41 will not be substantially destroyed or removed during insertion, but the device will merely lie in place suitably formed in a curvature as seen in FIGS. 7 and 9, to conform to the ridge line. The tube being flexible longitudinally as well as circumferentially or peripherally in cross section, will naturally conform to an arcuate contour of the alveolar ridge line in cross section.

It will be seen by the device and technique of the invention that a matrix of granular material which will not migrate, and which will stay in position, will provide a structure for tissue fiber migration and bone formation into a substantial and desirable ridge line which will provide aesthetically a desirable and natural face contour, and equally if not more important, provide a substantial ridge which will enable dentures to be optimally supported in the mouth. The dentures will have a matching receptacle trough which will be placed over the ridge in well known denture fashion.

The upper alveolar ridge is restored in the same manner using the same techniques and devices described above.

A further advantage of having a proper type ridge is the mandibular joint is maintained in its proper articulated relationship. The lower jaw is not thrown forward.

I claim:

1. The technique of implanting a flexible tissue matrix in an alveolar ridge in the edentulous state, comprising slitting the skin area over the said ridge, transversely of the ridge, inserting through said slit and along said ridge a tunneling tool comprising a rigid outer sheath and a telescoping inner rod, attaching to the inner rod at its end remote from the said slit a flexible device comprising an outer tube of porous, inert material containing particles of inert porous matrix material, attaching one end of said device to the end of the telescoping rod, withdrawing the rod through the outer sheath to a position over the alveolar ridge, and withdrawing the tunneling sheath through the slit, while maintaining the flexible device in place along the alveolar ridge.

2. The technique of claim 1 wherein the device is secured along the ridge by suturing the device to the alveolar ridge.

3. The technique of claim 1 wherein a plurality of slits are formed in the skin over the ridge and the tunneling tube is repetitively used to position the device along the ridge between the slits.

4. In a matrix for tissue regeneration and bone restorations of the human alveolar ridge having
   porous particles held in abutting relationship to one another by a flexible bag of a porous, inert material, wherein the bag conforms to the portion of the alveolar ridge on which the bag is positioned,
the improvement comprising
   forming the bag of an inner porous tube within an outer porous tube wherein
      (1) the pores of the inner tube are smaller than the size of the particles, and
      (2) the pores of the outer tube are substantially larger than the pores of the inner tube,
whereby tissue is permitted to grow more rapidly through the outer tube than through the inner tube.

5. A matrix of claim 4 having a plurality of outer tubes concentrially arranged, the tubes being of different porosity whereby tissue growth is selectively controlled through the tubes.

6. A matrix of claim 4 wherein the inner tube prevents particles having a size larger than the pores of the inner tube from migrating out through the tube.

* * * * *